United States Patent
Nomura et al.

(10) Patent No.: US 12,426,949 B2
(45) Date of Patent: Sep. 30, 2025

(54) DETECTION SYSTEM, CATHETER DEVICE, AND LASER ABLATION DEVICE

(71) Applicant: FURUKAWA ELECTRIC CO., LTD., Tokyo (JP)

(72) Inventors: Yoshiki Nomura, Tokyo (JP); Shunichi Matsushita, Tokyo (JP)

(73) Assignee: FURUKAWA ELECTRIC CO., LTD., Tokyo (JP)

( * ) Notice: Subject to any disclaimer, the term of this patent is extended or adjusted under 35 U.S.C. 154(b) by 647 days.

(21) Appl. No.: 17/099,938

(22) Filed: Nov. 17, 2020

(65) Prior Publication Data
US 2021/0068899 A1 Mar. 11, 2021

Related U.S. Application Data

(63) Continuation of application No. PCT/JP2019/021076, filed on May 28, 2019.

(30) Foreign Application Priority Data

Jun. 1, 2018 (JP) .................. 2018-106290

(51) Int. Cl.
*A61B 18/24* (2006.01)
*G01M 11/00* (2006.01)
(Continued)

(52) U.S. Cl.
CPC ............. *A61B 18/24* (2013.01); *G01M 11/31* (2013.01); *G02B 6/4246* (2013.01);
(Continued)

(58) Field of Classification Search
CPC .......... A61B 18/24; A61B 2017/00725; A61B 2018/00577; A61B 2034/2061; G01M 11/31; G02B 6/4246
(Continued)

(56) References Cited

U.S. PATENT DOCUMENTS 4,883,054 A * 11/1989 Fuller .................. G02B 6/4469
356/73.1
6,819,815 B1 * 11/2004 Corbalis .............. G02B 6/3588
385/16
(Continued)

FOREIGN PATENT DOCUMENTS

EP 3 851 061 A1 7/2021
JP 63-098507 U 6/1988
(Continued)

OTHER PUBLICATIONS

Yun, S.H., Bouma, B.E., Wavelength Swept Lasers, In: Drexler, W., Fujimoto, J.G. (eds) Optical Coherence Tomography. Biological and Medical Physics, Biomedical Engineering, Springer, Berlin, Heidelberg, pp. 359-377 (Year: 2008).*
(Continued)

*Primary Examiner* — Ahmed M Farah
(74) *Attorney, Agent, or Firm* — Oblon, McClelland, Maier &Neustadt, L.L.P.

(57) ABSTRACT

A detection system includes: at least one light source that outputs a plurality of test beams input to a proximal end portion side of an optical fiber and having different wavelengths and providing different bending losses of the optical fiber; at least one reflector that reflects each of the test beams propagating through the optical fiber, on a distal end portion side of the optical fiber; a plurality of light receiving units that receive a plurality of reflected beams each being a beam reflected by the at least one reflector, on the proximal end portion side; and a determination unit that, based on information about the reflected beams at the plurality of light receiving units, compares the information about the reflected beams with reference set values.

11 Claims, 6 Drawing Sheets

(51) Int. Cl.
*G02B 6/42* (2006.01)
*A61B 17/00* (2006.01)
*A61B 18/00* (2006.01)
*A61B 34/20* (2016.01)

(52) U.S. Cl.
CPC .............. *A61B 2017/00725* (2013.01); *A61B 2018/00577* (2013.01); *A61B 2034/2061* (2016.02)

(58) Field of Classification Search
USPC .......................................................... 606/15
See application file for complete search history.

(56) References Cited

U.S. PATENT DOCUMENTS

| | | | |
|---|---|---|---|
| 12,184,038 B2 * | 12/2024 | Nomura | H01S 5/005 |
| 2004/0165810 A1 | 8/2004 | Fujita | |
| 2007/0116415 A1 | 5/2007 | Kobayashi | |
| 2011/0109898 A1 * | 5/2011 | Froggatt | G01B 11/168 356/73.1 |
| 2012/0323075 A1 | 12/2012 | Younge et al. | |
| 2014/0139337 A1 | 5/2014 | Piper, Sr. et al. | |
| 2015/0346054 A1 | 12/2015 | L'Heureux et al. | |
| 2016/0103017 A1 | 4/2016 | Hung | |
| 2016/0123837 A1 * | 5/2016 | Chen | G01M 11/3172 356/73.1 |
| 2016/0360951 A1 | 12/2016 | Hane | |
| 2017/0100196 A1 | 4/2017 | Takayama et al. | |
| 2017/0149496 A1 | 5/2017 | Perron et al. | |
| 2017/0196479 A1 | 7/2017 | Liu et al. | |
| 2017/0276475 A1 * | 9/2017 | Morino | G01B 11/14 |
| 2018/0224269 A1 | 8/2018 | Takayama et al. | |
| 2020/0397312 A1 * | 12/2020 | Ben Oren | G16H 40/63 |
| 2022/0003634 A1 * | 1/2022 | Nomura | G01M 11/33 |

FOREIGN PATENT DOCUMENTS

| | | | | |
|---|---|---|---|---|
| JP | 03-111039 A | 5/1991 | | |
| JP | 2001-169998 A | 6/2001 | | |
| JP | 2002-291764 A | 10/2002 | | |
| JP | 2015-181643 A | 10/2015 | | |
| WO | WO-2008118541 A3 * | 12/2008 | ......... | G01D 5/35303 |
| WO | WO-2016194059 A1 * | 12/2016 | ......... | A61B 1/00071 |
| WO | WO 2017/060956 A1 | 4/2017 | | |

OTHER PUBLICATIONS

Morgan et al., "Wavelength dependence of bending loss in monomode optical fibers: effect of the fiber buffer coating", 1990, Optical Society of America, vol. 15, Issue 17, pp. 947-949. (Year: 1990).*
Li et al., "Distributed fiber-optic bi-directional strain-displacement sensor modulated by fiber bending loss", 2004, Elsevier, vol. 111, Issues 2-3, pp. 236-239 (Year: 2004).*
Kapron et al., "Radiation Losses in Glass Optical Waveguides", 1970, American Institute of Physics, vol. 17, Issue 10, pp. 423-425 (Year: 1970).*
Lowdermilk et al., "Optical Coatings for Laser Fusion Application", 1980, Elsevier, vol. 73, Issue 1, pp. 155-166 (Year: 1980).*
Greer, CCEA as Physics Student Unit Guide: Unit 2 Waves, Photons and Medical Physics, May 3, 2013, Hodder Education, p. 95 (Year: 2013).*
International Search Report issued Aug. 13, 2019 in PCT/JP2019/021076 filed on May 28, 2019, 1 page.
Extended European Search Report issued Jan. 31, 2022 in European Patent Application No. 19810570.2, 8 pages.
Office Action issued Sep. 16, 2023 in Chinese Patent Application No. 201980035534.9 with English machine translation, 20 pages.
European Office Action report dated Feb. 16, 2024 in corresponding European Application No. 19810570.2, 5 pages.
Min Cen et al., Advanced Fault-Monitoring Scheme for Ring-Based Long-Reach Optical Access Networks, Journal of Lightwave Technology, vol. 35, No. 10, May 15, 2017, pp. 1876-1886.

* cited by examiner

FIG.4

DETECTION SYSTEM, CATHETER DEVICE, AND LASER ABLATION DEVICE

CROSS-REFERENCE TO RELATED APPLICATION(S)

This application is a continuation of International Application No. PCT/JP2019/021076, filed on May 28, 2019, which claims the benefit of priority of the prior Japanese Patent Application No. 2018-106290, filed on Jun. 1, 2018, the entire contents of which are incorporated herein by reference.

BACKGROUND

The present disclosure relates to a detection system, a catheter device, and a laser ablation device.

Background

There is known a technique to insert a catheter into which an optical fiber is inserted into a patient's body to perform treatment. Such a technique is used for, for example, laser ablation devices. In a laser ablation device, a catheter is inserted into a patient's body to output an ablation laser beam from a distal end of an optical fiber and irradiate a target area such as an affected area, for treatment.

In the related art, techniques are disclosed to detect the curvatures of or estimate curved shapes of tubular bodies, such as endoscopes, inserted into bodies (see Patent Japanese Laid-open Patent Publication Nos. 2001-169998 and 2015-181643).

SUMMARY

There is a need for providing a detection system, a catheter device, and a laser ablation device that are configured to detect a state of an optical fiber and a state around the optical fiber.

According to an embodiment, a detection system includes: at least one light source that outputs a plurality of test beams input to a proximal end portion of an optical fiber and having different wavelengths and providing different bending losses of the optical fiber; at least one reflector that reflects each of the test beams propagating through the optical fiber, near a distal end portion of the optical fiber; a plurality of light receiving units that receive a plurality of reflected beams each being a beam reflected by the at least one reflector, near the proximal end portion; and a determination unit that, based on information about the reflected beams at the plurality of light receiving units, compares the information about the reflected beams with reference set values.

DETAILED DESCRIPTION

In the related art, when the optical fiber inserted into the catheter bends in the body, the propagation loss of the optical fiber may increase, reducing the intensity of ablation laser beam output from the distal end of the optical fiber, but depending on the degree of bending, the reduction in strength may cause no problem. On the other hand, when the optical fiber breaks in the body, ablation laser beam is not output from the distal end of the optical fiber, and further the optical fiber does not recover from the breakage. When the optical fiber breaks in the body, incomplete treatment is obtained or ablation at a portion other than the target area may occur. In order to prevent this, there has been a demand for a technique to suitably detect bending or breakage of optical fiber. However, a technique for detecting the state of optical fiber, for example, a technique for separately detecting bending and breakage has not been disclosed.

Furthermore, there has been a demand for detecting a state of an environment around an optical fiber, for example, external pressure or temperature, such as blood pressure or body temperature, in addition to a state of the optical fiber, when a catheter including the optical fiber is inserted into a living body, such as a human body.

Hereinafter, embodiments of the present disclosure will be described in detail with reference to the accompanying drawings. Note that the present disclosure is not limited to the embodiments described below. Furthermore, in the description of the drawings, the same or corresponding elements are appropriately denoted by the same reference numerals.

Figure 1:
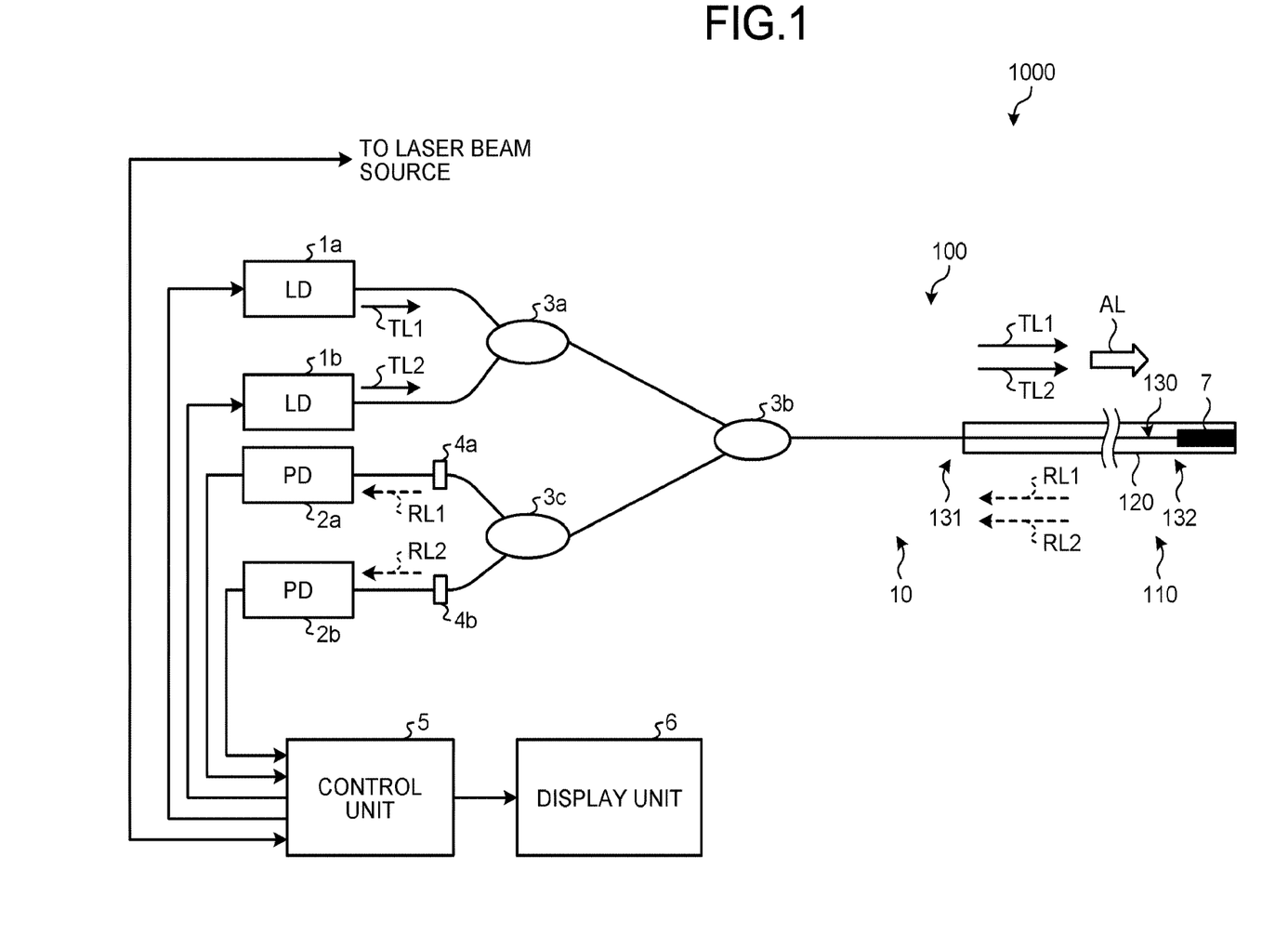
FIG. 1 is a schematic diagram illustrating a schematic configuration of a laser ablation device according to an embodiment.

FIG. 1 is a schematic diagram illustrating a schematic configuration of a laser ablation device according to an embodiment. The laser ablation device 1000 includes a laser beam source, which is not illustrated, an optical multiplexer/demultiplexer for an ablation laser, which is not illustrated, and a catheter device 100.

The laser beam source includes a laser beam source such as an optical fiber laser and outputs an ablation laser beam AL. The optical multiplexer/demultiplexer for an ablation laser multiplexes the laser beam AL with a first test beam and a second test beam which are described below, and outputs an obtained beam. In the present embodiment, the optical multiplexer/demultiplexer for an ablation laser is placed between an optical multiplexer/demultiplexer 3a and an optical multiplexer/demultiplexer 3b, which are described later, but may be placed downstream the optical multiplexer/demultiplexer 3b. The optical multiplexer/demultiplexer for an ablation laser may be configured to multiplex a plurality of beams spatially or by using an optical combiner or the like.

The catheter device 100 includes a detection system 10 for optical fiber and a catheter portion 110. The catheter portion 110 is at least partially inserted into a patient's body. The catheter portion 110 includes a catheter body 120 that is formed of a flexible material such as resin, and an optical fiber 130 at least partially inserted into a lumen of the catheter body 120.

The optical fiber 130 includes a proximal end portion 131 and a distal end portion 132. The optical fiber 130 includes, for example, but is not particularly limited to, step-index or graded-index multi-mode optical fiber or multi-core optical fiber having a plurality of concentric cores. Furthermore, in a case where the catheter device 100 is a medical catheter device to be inserted into a blood vessel, the optical fiber 130 preferably has, but is not particularly limited to, a small diameter, for example, a core diameter of not more than 105 μm and a clad diameter of not more than 125 μm.

The detection system 10 includes a plurality of light sources and a plurality of light receiving units. In the present embodiment, the detection system 10 includes a laser diode (LD) 1a that has a function of a first light source, a LD 1b that has a function of a second light source, a photodiode (PD) 2a that has a function of a first light receiving unit, and a PD 2b that has the function of a second light receiving unit. Furthermore, the detection system 10 includes optical multiplexers/demultiplexers 3a, 3b, and 3c and bandpass filters 4a and 4b. Still furthermore, the detection system 10 includes a control unit 5, a display unit 6, and a fiber Bragg grating (FBG) 7. The FBG7 is provided near the distal end portion 132 of the optical fiber 130 and functions as a reflector.

The LD 1a outputs the first test beam TL1 having a predetermined wavelength from an optical fiber represented by a solid line. The LD 1b outputs the second test beam TL2 from an optical fiber represented by a solid line. The second test beam TL2 has a wavelength at which a bending loss of the optical fiber 130 is larger than a bending loss at a wavelength of the first test beam TL1. In other words, the first test beam TL1 and the second test beam TL2 have different wavelengths and provide different bending losses of the optical fiber 130. Here, the wavelength $\lambda 2$ of the second test beam TL1 ($\lambda 2 = n\lambda 1$, n is an integer of 2 or more). The wavelength $\lambda 1$ of the first test beam TL1 and the wavelength $\lambda 2$ of the second test beam TL2 are limited by a reflection wavelength bandwidth in the FBG7 or the like as the reflector. Specifically, for example, when the reflection wavelength bandwidth is 630 to 660 nm, the wavelength $\lambda 1$ of the first test beam TL1 is preferably 630 to 660 nm, and the wavelength $\lambda 2$ of the second test beam TL2 is preferably 1260 to 1320 nm. This improves the possibility of sharing the FGB7, a reflecting film or the like.

Figure 2:
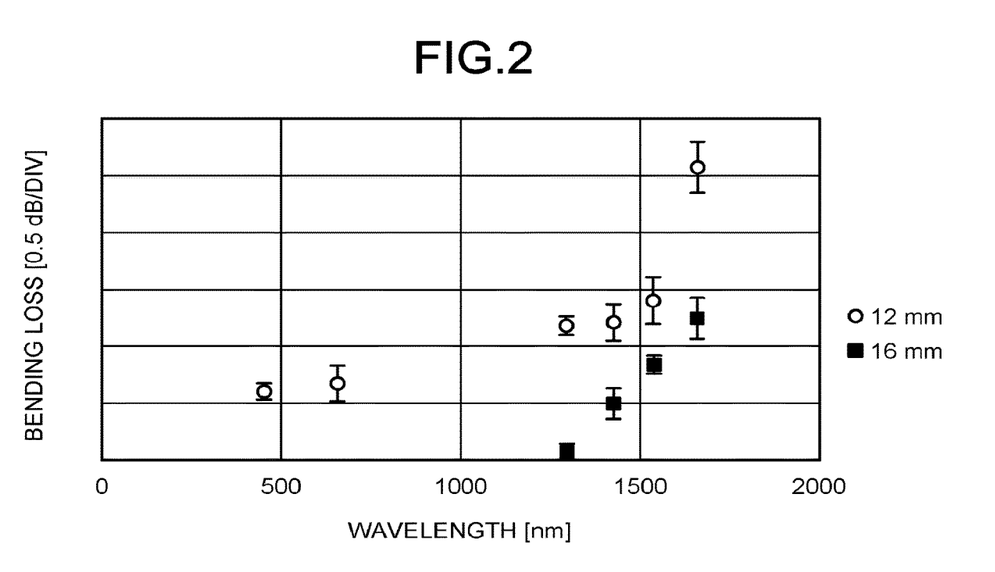
FIG. 2 is a graph illustrating an example of a bending loss characteristic of an optical fiber.

FIG. 2 is a graph illustrating an example of a bending loss characteristic per turn of an optical fiber. The bending loss of an optical fiber is defined by an amount of increase in transmission loss per turn when the optical fiber is bent, for example, with a predetermined bend radius. Here, one turn means a state in which the optical fiber is wound around once with a predetermined bend radius.

In FIG. 2, white circles represent a bend radius of 6 mm (diameter of 12 mm), and black squares represent a bend radius of 8 mm (diameter of 16 mm). Furthermore, an error bar represents a standard deviation calculated on the basis of 10 data points around a wavelength of a white circle or black square.

As illustrated in FIG. 2, the bending loss of an optical fiber generally increases with increasing wavelength. Therefore, making the wavelength of the second test beam TL2 longer than the wavelength of the first test beam TL1 can increase the bending loss in the second test beam TL2 relative to the bending loss in the first test beam TL1, in the optical fiber 130.

When the bending loss in the second test beam TL2 is larger than the bending loss in the first test beam TL1, in the optical fiber 130, it can be said that the second test beam TL2 is more sensitive to the bending of the optical fiber 130 than the first test beam TL1. Similarly, it can be said that the first test beam TL1 is less sensitive to the bending of the optical fiber 130 than the second test beam TL2. Note that the wavelength of the first test beam TL1 is preferably not more than 1300 nm, and more preferably, is in the visible light wavelength range.

In an example of the wavelength $\pi 1$ of the first test beam TL1 and the wavelength $\lambda 2$ of the second test beam TL2, the wavelength $\lambda 1$ can be set in a 1300 nm band and the wavelength $\lambda 2$ can be set in a 1500 nm band. It can be seen from FIG. 2 that the bending loss is smaller in the 1300 nm band than in the 1500 nm band (note that the band has a bandwidth of 100 nm, for example, the 1500 nm band has a bandwidth of 1500 to 1600 nm).

In another example, it is also possible to set the wavelength $\lambda 1$ in a 1000 nm band and the wavelength $\lambda 2$ in a 1500 nm band. In this case, as will be described later, the bandpass filter 4a located upstream the PD 2a that receives a reflected beam from the first test beam TL1 is not required.

Returning to FIG. 1, the optical multiplexer/demultiplexer 3a multiplexes the first test beam TL1 and the second test beam TL2 at a predetermined ratio, for example, a ratio of 1:1 and outputs the multiplexed beam to the optical multiplexer/demultiplexer for an ablation laser via an optical fiber represented by a solid line. The optical multiplexer/demultiplexer for an ablation laser multiplexes the input first test beam TL1 and second test beam TL2 with the laser beam AL and outputs the multiplexed beam to the optical multiplexer/demultiplexer 3b via the optical fiber represented by the solid line. The optical multiplexer/demultiplexer 3b outputs the input first test beam TL1, second test beam TL2, and laser beam AL to the optical fiber 130 via an optical fiber represented by a solid line. Therefore, the first test beam TL1, the second test beam TL2, and the laser beam AL are input to the proximal end portion 131 of the optical fiber 130 and propagate through the optical fiber 130.

The FBG7 is provided near the distal end portion 132 of the optical fiber 130 and is fusion-spliced, for example, to the distal end portion 132 of the optical fiber 130. The FBG7 reflects the first test beam TL1 and the second test beam TL2 propagating through the optical fiber 130 and transmits the laser beam AL. Therefore, the laser beam AL is output from the distal end portion 132 of the optical fiber 130 (a distal end portion of the catheter portion 110).

A first reflected beam RL1 that is a reflected beam from the first test beam TL1 and a second reflected beam RL2 that is a reflected beam from the second test beam TL2 propagate through the optical fiber 130 in the opposite direction to the first test beam TL1 and the second test beam TL2 and are output from the proximal end portion 131 to the optical multiplexer/demultiplexer 3b. The optical multiplexer/demultiplexer 3b outputs the input first reflected beam RL1 and second reflected beam RL2 to the optical multiplexer/demultiplexer 3c.

The optical multiplexer/demultiplexer 3c demultiplexes the first reflected beam RL1 and the second reflected beam RL2 and outputs the first reflected beam RL1 to the bandpass filter 4a via an optical fiber represented by a solid line. Furthermore, the optical multiplexer/demultiplexer 3c outputs the second reflected beam RL2 to the bandpass filter 4b via an optical fiber represented by a solid line. The bandpass filter 4a is designed to selectively transmit light having a wavelength of the first reflected beam RL1 and hardly transmit light having a wavelength of the second reflected beam RL2. Thus, a component of the second reflected beam RL2 that cannot be demultiplexed by the optical multiplexer/demultiplexer 3c is blocked by the bandpass filter 4a. For the same reason, the bandpass filter 4b is designed to selectively transmit light having a wavelength of the second reflected beam RL2 and hardly transmit light having a wavelength of the first reflected beam RL1.

Furthermore, the bandpass filters 4a and 4b may be configured to also block light having a wavelength of the laser beam AL. When the laser beam AL has high power, there is a possibility that light that is obtained by Fresnel reflection of the laser beam AL due to air at an end portion of the FBG7 reaches the PDs 2a and 2b. The bandpass filters 4a and 4b may be used to remove this reflection.

The PD 2a receives the first reflected beam RL1 having passed through the bandpass filter 4a and outputs a current signal according to the received light intensity of the first reflected beam RL1. The PD 2b receives the second reflected beam RL2 having passed through the bandpass filter 4b and outputs a current signal according to the received light intensity of the second reflected beam RL2.

The bandpass filters 4a and 4b may not be required depending on configuration. For example, when the optical multiplexer/demultiplexer 3b employs a WDM coupler, the bandpass filters 4a and 4b are not required in principle due to high extinction ratio and efficient demultiplexing.

Alternatively, consider that of the PDs 2a and 2b, the PD 2a employs a Si photodiode and the PD 2b employs an InGaAs photodiode. In general, Si has extremely poor sensitivity at a wavelength of 1100 nm band or more, and therefore, for example, if the wavelength $\lambda 1$ of the first test beam TL1 is set in a 800 nm band and the wavelength $\lambda 2$ of the second test beam TL2 is set in the 1500 nm band, the bandpass filter 4a is not required for the PD 2a, which is an Si photodiode that receives the first reflected beam RL1 in the 800 nm band.

Note that the optical multiplexers/demultiplexers 3a, 3b, and 3c are preferably constituted by a 50:50 TAP coupler, an asymmetric TAP coupler, a WDM coupler, or a combination thereof.

The control unit 5 has a function of a determination unit. The control unit 5 includes a calculation unit and a storage unit. The calculation unit performs various calculation processes for achieving controls executed by the control unit 5 and the functions of the control unit and includes, for example, a central processing unit (CPU), a field-programmable gate array (FPGA), or both of the CPU and the FPGA. The storage unit includes a portion constituted by, for example, a read only memory (ROM), and the portion stores various programs and data used by the calculation unit to perform the calculation processes. In addition, the storage unit includes a portion constituted by, for example, a random access memory (RAM), and the portion is used such as for a work space when the calculation unit performs a calculation process or for storing results of the calculation processes of the calculation unit.

Furthermore, the control unit 5 includes an input unit that receives an input of a current signal from the PDs 2a and 2b or an operation state signal indicating an operation state of the laser beam source from the laser beam source. Specifically, the PDs 2a and 2b and the bandpass filters 4a and 4b allow the control unit 5 to acquire, as information about the reflected beams, at least one of the received light intensity and the reflection wavelength of each of the first reflected beam RL1 and the second reflected beam RL2. In other words, the control unit 5 monitors a shift in wavelength of a reflected beam caused by the FBG7. Thus, in addition to the breakage or an amount of bending, by acquiring information from the reflected beam reflected by the reflector such as FBG7, the temperature (body temperature) or pressure (blood pressure) at a portion to which the catheter portion 110 is inserted can be monitored.

Furthermore, the control unit 5 includes an output unit, and the output unit outputs, on the basis of the results of the various calculation processes, driving current to the LDs 1a and 1b, a laser beam output stop signal for stopping output of the laser beam AL from the laser beam source, and an instruction signal to the display unit 6.

The display unit 6 is a portion that displays characters and symbols for notifying an operator of the laser ablation device 1000 of various information, in response to an instruction signal from the control unit 5 and includes, for example, a liquid crystal display.

First Control Example

Figure 3:
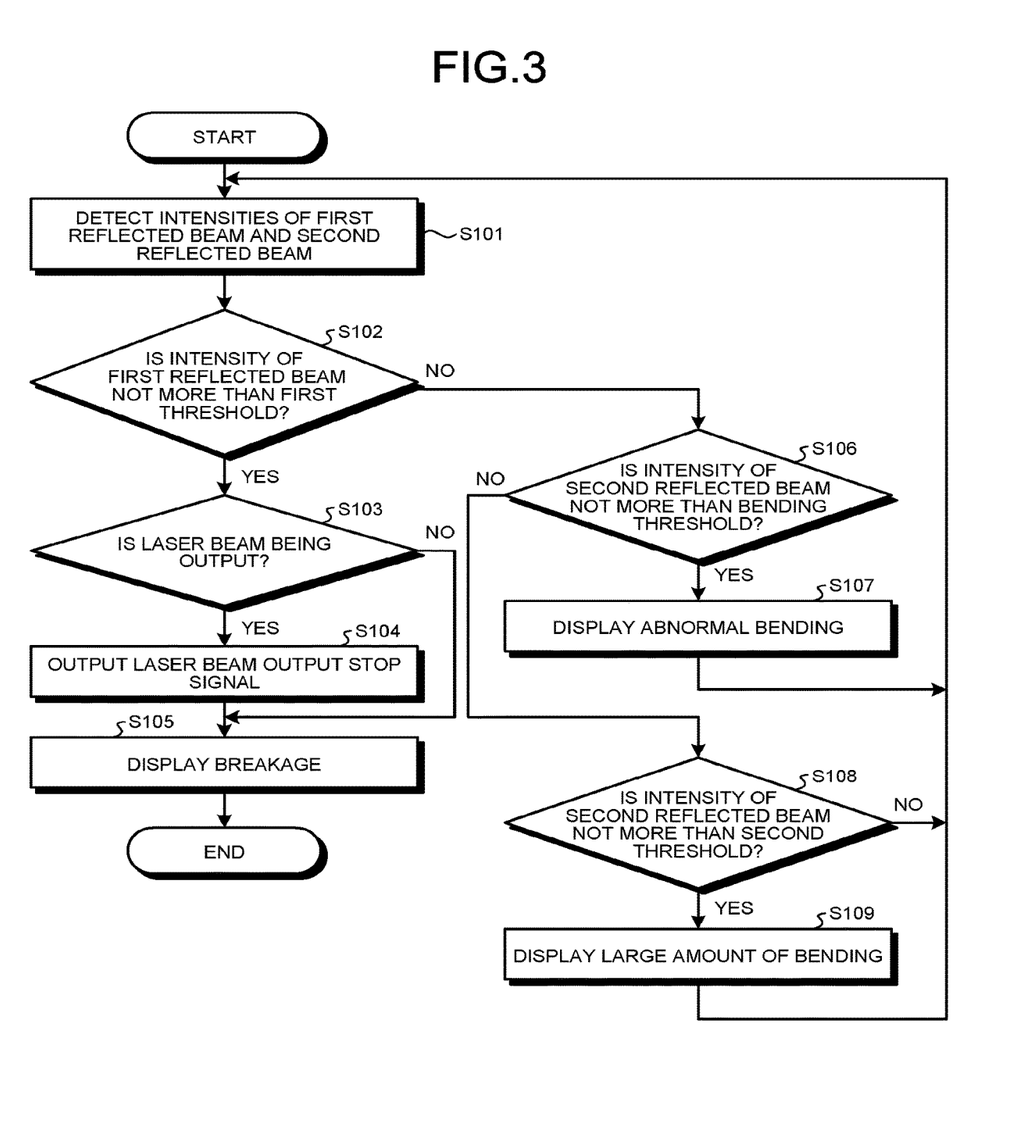
FIG. 3 is a flowchart of a first control example.

Next, an example of control executed by the control unit 5 will be described. FIG. 3 is a flowchart of a first control example. This control process is performed in a state where the control unit 5 supplies the driving current to the LDs 1a and 1b, and the first test beam TL1 and the second test beam TL2 are output.

Firstly, in Step S101, the control unit 5 detects, on the basis of current signals from the PDs 2a and 2b, the received light intensity (hereinafter, appropriately referred to as intensity) of the first reflected beam RL1 and the received light intensity of the second reflected beam RL2. Subsequently, in Step S102, the control unit 5 determines whether the intensity of the first reflected beam RL1 is not more than a first threshold. Note that the first threshold as reference set value is a value that is small to the extent to determine the breakage of the optical fiber 130. If the intensity of the first reflected beam RL1 is not more than the first threshold (Step S102: Yes), the control proceeds to Step S103. At this time, the control unit 5 determines that the optical fiber 130 is broken.

In Step S103, the control unit 5 determines whether the laser beam AL is being output from the laser beam source, on the basis of an operation state signal from the laser beam source. If the laser beam AL is being output (Step S103: Yes), the control proceeds to Step S104. In Step S104, the control unit 5 outputs the laser beam output stop signal to the laser beam source. Therefore, the output from the laser beam AL is stopped. If the laser beam AL is not output (Step S103: No) and after the end of Step S104, the control proceeds to Step S105.

In Step S105, the control unit 5 outputs an instruction signal to the display unit 6 to display characters, symbols or the like for notifying of the breakage of the optical fiber 130. Then, the control ends.

On the other hand, if the intensity of the first reflected beam RL1 is larger than the first threshold (Step S102: No), the control proceeds to Step S106. At this time, the control unit 5 determines that the optical fiber 130 is not broken.

In Step S106, the control unit 5 determines whether the intensity of the second reflected beam RL2 is not more than a predetermined bending threshold. If the intensity of the second reflected beam RL2 is not more than the predetermined bending threshold (Step S106: Yes), the control proceeds to Step S107. Here, the bending threshold is a reference set value used when the catheter portion 110 is inserted into an unexpected wrong portion. Note that reference set values are stored in the storage unit of the control unit 5 in the form of an array or the like, as a table or function expressions. This configuration enables the control unit 5 to calculate the amount of bending of the optical fiber 130 on the basis of an input value, and the magnitude of the amount of bending can be determined by comparison with a reference set value relating to the amount of bending. Here, the control unit 5 determines that the optical fiber 130 is bent with an abnormal amount of bending that is equal to or larger than a predictable amount of bending. Here, the amount of bending is an amount indicating the degree of bending of the optical fiber 130. The amount of bending can be expressed as, for example, the amount of an increase in transmission loss (bending loss) caused by bending of the optical fiber 130 and can be expressed as the total bending loss occurring over the entire length of the optical fiber 130. In the present embodiment, the bending threshold is a value corresponding to a light intensity indicated when, for example, a bending loss of 1 dB is given.

In Step S107, the control unit 5 outputs an instruction signal to the display unit 6 to display characters, symbols or the like for notifying that the optical fiber 130 has an abnormal amount of bending. Then, the control returns to Step S101.

On the other hand, if the intensity of the second reflected beam RL2 is larger than the predetermined bending threshold (Step S106: No), the control proceeds to Step S108. In Step S108, the control unit 5 determines whether the intensity of the second reflected beam RL2 is not more than a second threshold. If the intensity of the second reflected beam RL2 is not more than the second threshold (Step S108: Yes), the control proceeds to Step S109. At this time, the control unit 5 determines that the optical fiber 130 is bent with an amount of bending not less than a predetermined amount of bending. Here, the definition of the amount of bending is the same as the definition described above.

In Step S109, the control unit 5 outputs an instruction signal to the display unit 6 to display characters, symbols or the like for notifying that the optical fiber 130 has a large amount of bending. Then, the control returns to Step S101. On the other hand, if the intensity of the second reflected beam RL2 is larger than the second threshold (Step S108: No), the control returns to Step S101.

In the first control example, when the received light intensity of the first test beam TL1 that is less sensitive to the bending of the optical fiber 130 than the second test beam TL2 is not more than the first threshold, it is determined that the optical fiber 130 is broken. On the other hand, when the received light intensity of the first test beam TL1 is larger than the first threshold, it is determined that the optical fiber 130 is not broken. Therefore, the breakage and the bending of the optical fiber 130 can be effectively distinguished and detected. The first threshold as the reference set value used for the determination is set to a value that is small to the extent to determine the breakage of the optical fiber 130 on the basis of a result of a preliminary experiment or the like and is stored in the storage unit of the control unit 5.

In addition, in the first control example, when breakage of the optical fiber 130 is determined and the laser beam AL is also being output, the output of the laser beam AL is stopped. Thus, the effect of preventing the laser beam AL from being unintentionally output from the broken portion of the optical fiber 130 can be obtained. Furthermore, when it is determined that the optical fiber 130 is broken, the effect can be obtained that the operator of the laser ablation device 1000 can be notified of the breakage of the optical fiber 130.

Furthermore, assuming that the catheter portion 110 is inserted into a human body or a living body, the airway, esophagus, or blood vessel have sharply bending portions in common. Therefore, normally predictable bending losses of the optical fiber 130 in a passage route in the catheter portion 110 can be almost derived. From this point, when a bending loss that is larger than a normally predictable bending loss of the optical fiber 130 in a passage route is generated, there is a possibility that the catheter portion 110 has been inserted into a wrong portion into which no insertion of the catheter portion 110 is expected. Therefore, in the first control example, when the received light intensity of the first reflected beam RL1 is larger than the first threshold and the intensity of the second reflected beam RL2 is not more than the bending threshold, it can be detected whether the catheter portion 110 is inserted in a wrong direction with sharp bending of the optical fiber 130 that exceeds the predictable amount of bending or whether any portion of the inserted portion is caught and sharply bent. Therefore, an effect can be obtained that when it is determined that the catheter portion is bent with the abnormal amount of bending, the operator can be notified of this and thus, the safety in use of the catheter portion 110 can be improved. Note that the bending threshold that is a reference set value for the determination is set to a value corresponding to an abnormal amount of bending of the optical fiber 130 that the operator is to be notified of, on the basis of a result of a preliminary experiment or the like, and the bending threshold is stored in the storage unit of the control unit 5.

Furthermore, in the first control example, an effect can be obtained that when the received light intensity of the first test beam TL1 is larger than the first threshold and the intensity of the second reflected beam RL2 is larger than the bending threshold and is not more than the second threshold, it is determined that the optical fiber 130 is bent with the amount of bending that is not less than the predetermined amount of bending, and the operator can be notified of this. The second threshold that is a reference set value for the determination is set to a value corresponding to an amount of bending of the optical fiber 130 that the operator is to be notified of, on the basis of a result of a preliminary experiment or the like, and the bending threshold is stored in the storage unit of the control unit 5.

Second Control Example

Figure 4:
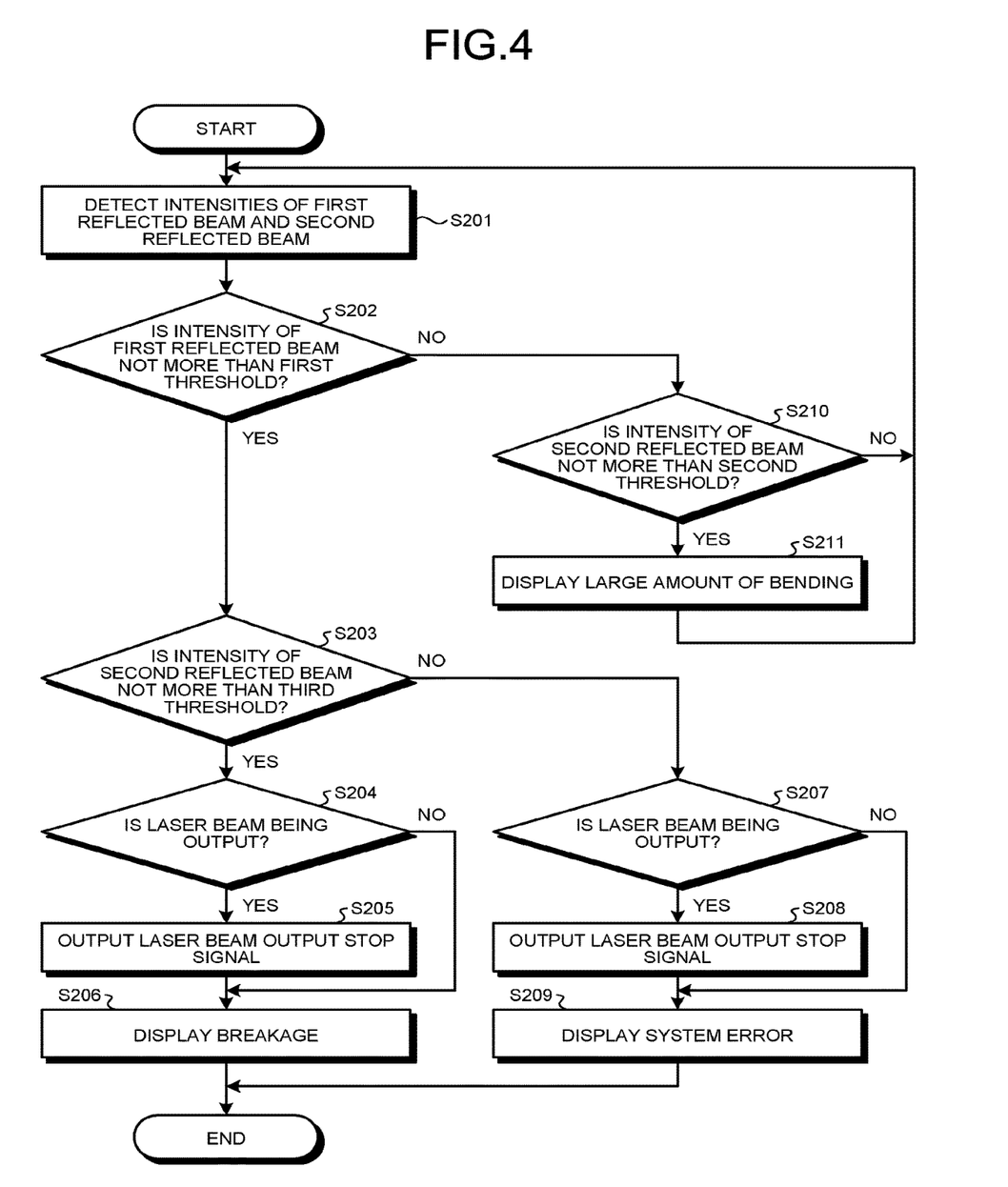
FIG. 4 is a flowchart of a second control example.

FIG. 4 is a flowchart of a second control example. This control process is performed in a state where the control unit 5 supplies the driving current to the LDs 1a and 1b, and the first test beam TL1 and the second test beam TL2 are output.

Firstly, in Step S201, the control unit 5 detects the intensity of the first reflected beam RL1 and the intensity of the second reflected beam RL2, as in Step S101 of the first control example. Subsequently, in Step S202, the control unit 5 determines whether the intensity of the first reflected beam RL1 is not more than the first threshold, as in Step S102 of the first control example. If the intensity of the first reflected beam RL1 is not more than the first threshold (Step S202: Yes), the control proceeds to Step S203. At this time, the control unit 5 determines that the optical fiber 130 is broken.

Subsequently, in Step S203, the control unit 5 determines whether the intensity of the second reflected beam RL2 is not more than a third threshold. If the intensity of the second reflected beam RL2 is not more than the third threshold (Step S203: Yes), the control proceeds to Step S204. At this time, the control unit 5 maintains the determination that the optical fiber 130 is broken.

In Step S204, the control unit 5 determines whether the laser beam AL is being output, as in Step S103 of the first control example. If the laser beam AL is being output (Step S204: Yes), the control proceeds to Step S205. In Step S205, the control unit 5 outputs the laser beam output stop signal to the laser beam source, as in Step S104 of the first control example. If the laser beam AL is not output (Step S204: No) or after the end of Step S205, the control proceeds to Step S206.

In Step S206, the control unit 5 causes the display unit 6 to display characters or symbols for notifying of the breakage of the optical fiber 130, as in Step S105 of the first control example. Then, the control ends.

On the other hand, if the intensity of the second reflected beam RL2 is larger than the third threshold (Step S203: No), the control proceeds to Step S207. At this time, the control unit 5 changes the determination that the optical fiber 130 is broken to a determination that a system error has occurred in the detection system 10, the catheter device 100, or the laser ablation device 1000.

In Step S207, the control unit 5 determines whether the laser beam AL is being output. If the laser beam AL is being output (Step S207: Yes), the control proceeds to Step S208. In Step S208, the control unit 5 outputs the laser beam output stop signal to the laser beam source. If the laser beam AL is not output (Step S207: No) or after the end of Step S208, the control proceeds to Step S209.

In Step S209, the control unit 5 outputs an instruction signal to the display unit 6 to display characters, symbols or the like for notifying of occurrence of a system error. Then, the control ends.

On the other hand, if the intensity of the first reflected beam RL1 is larger than the first threshold (Step S202: No), the control proceeds to Step S210. At this time, the control unit 5 determines that the optical fiber 130 is not broken.

Subsequently, in Step S210, the control unit 5 determines whether the intensity of the second reflected beam RL2 is not more than the second threshold, as in Step S108 of the first control example. If the intensity of the second reflected beam RL2 is not more than the second threshold (Step S210: Yes), the control proceeds to Step S211. At this time, the control unit 5 determines that the optical fiber 130 is bent with an amount of bending not less than a predetermined amount of bending.

In Step S211, the control unit 5 outputs an instruction signal to the display unit 6 to display characters, symbols or the like for notifying that the optical fiber 130 has a large amount of bending. Then, the control returns to Step S201. On the other hand, if the intensity of the second reflected beam RL2 is larger than the second threshold (Step S210: No), the control returns to Step S201.

In the second control example, various effects similar to those of the first control example can be obtained. Furthermore, in the second control example, when the received light intensity of the first reflected beam RL1 is not more than the first threshold, it is determined that the optical fiber 130 is broken. However, when the received light intensity of the second reflected beam RL2 is larger than the third threshold, the determination that the optical fiber 130 is broken is changed to a determination that a system error has occurred in the detection system 10, the catheter device 100, or the laser ablation device 1000. When the received light intensity of the first reflected beam RL1 that is less sensitive to the bending of the optical fiber 130 is not more than the first threshold but the received light intensity of the second reflected beam RL2 that is sensitive to the bending of the optical fiber 130 is larger than the third threshold, it can be considered that such a state does not correspond to the state where the optical fiber 130 is bent or broken but has a situation where some kind of system error has occurred. Therefore, in the second control example, it is determined that a system error has occurred, and the operator can be notified of the system error. The third threshold that is a reference set value for the determination is set to the same value as the second threshold, for example and is stored in the storage unit of the control unit 5.

Third Control Example

Figure 5:
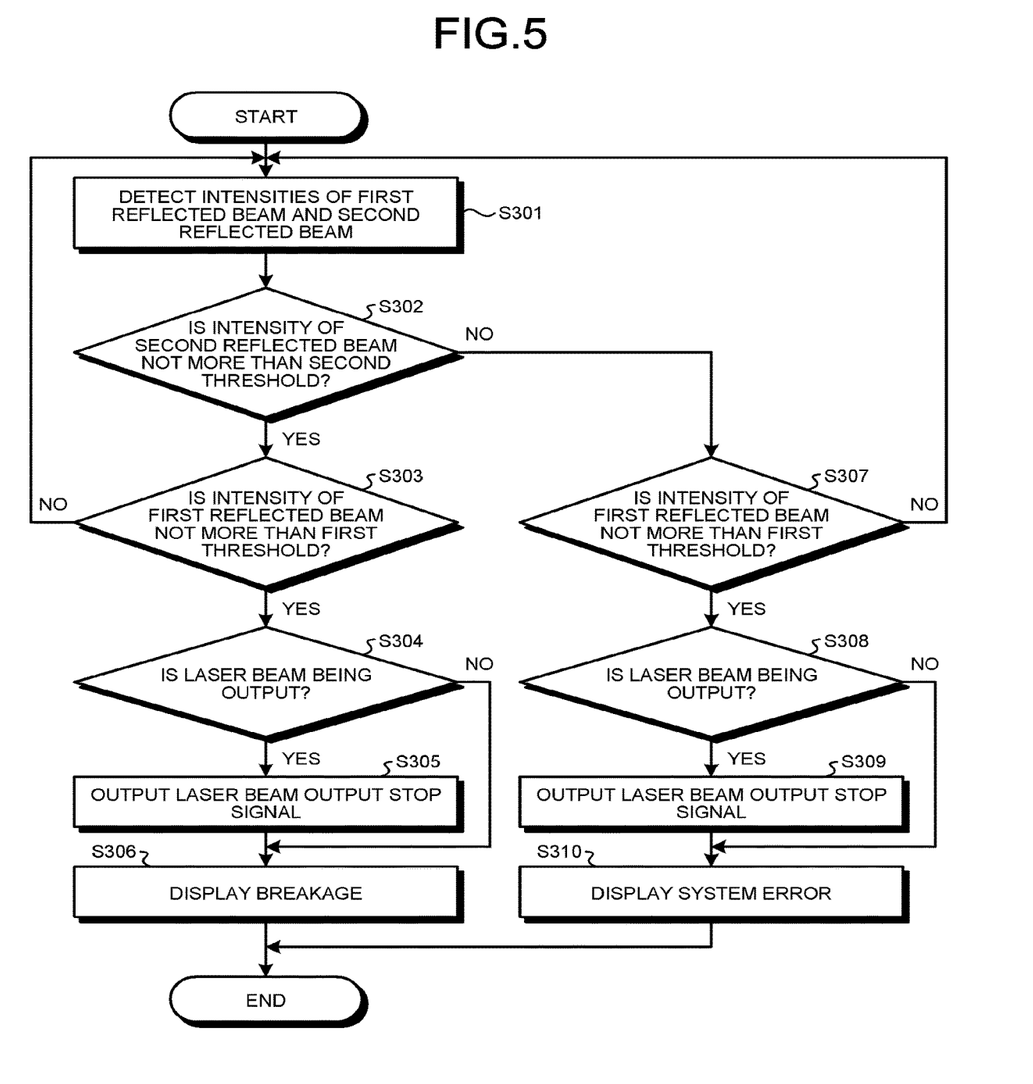
FIG. 5 is a flowchart of a third control example.

FIG. 5 is a flowchart of a third control example. This control process is performed in a state where the control unit 5 supplies the driving current to the LDs 1a and 1b, and the first test beam TL1 and the second test beam TL2 are output.

Firstly, in Step S301, the control unit 5 detects the intensity of the first reflected beam RL1 and the intensity of the second reflected beam RL2. Subsequently, in Step S302, the control unit 5 determines whether the intensity of the second reflected beam RL2 is not more than the second threshold. If the intensity of the second reflected beam RL2 is not more than the second threshold (Step S302: Yes), the control proceeds to Step S303. At this time, the control unit 5 determines that the optical fiber 130 is bent with an amount of bending not less than a predetermined amount of bending.

Subsequently, in Step S303, the control unit 5 determines whether the intensity of the first reflected beam RL1 is not more than the first threshold. If the intensity of the first reflected beam RL1 is not more than the first threshold (Step S303: Yes), the control proceeds to Step S304. At this time, the control unit 5 changes the determination that the optical fiber 130 is bent with an amount of bending not less than a predetermined amount of bending to a determination that the optical fiber 130 is broken.

In Step S304, the control unit 5 determines whether the laser beam AL is being output. If the laser beam AL is being output (Step S304: Yes), the control proceeds to Step S305. In Step S305, the control unit 5 outputs the laser beam output stop signal to the laser beam source. If the laser beam AL is not output (Step S304: No) or after the end of Step S305, the control proceeds to Step S306.

In Step S306, the control unit 5 causes the display unit 6 to display characters, symbols or the like for notifying of the breakage of the optical fiber 130. Then, the control ends.

Note that If the intensity of the first reflected beam RL1 is larger than the first threshold (Step S303: No), the control returns to Step S301. At this time, the control unit 5 maintains the determination that the optical fiber 130 is bent with an amount of bending not less than a predetermined amount of bending.

On the other hand, if the intensity of the second reflected beam RL2 is larger than the second threshold (Step S302: No), the control proceeds to Step S307. In Step S307, the control unit 5 determines whether the intensity of the first reflected beam RL1 is not more than the first threshold. If the intensity of the first reflected beam RL1 is not more than the first threshold (Step S307: Yes), the control proceeds to Step S308. At this time, the control unit 5 determines that a system error has occurred in the detection system 10, the catheter device 100, or the laser ablation device 1000.

In Step S308, the control unit 5 determines whether the laser beam AL is being output. If the laser beam AL is being output (Step S308: Yes), the control proceeds to Step S309. In Step S309, the control unit 5 outputs the laser beam output stop signal to the laser beam source. If the laser beam AL is not output (Step S308: No) or after the end of Step S309, the control proceeds to Step S310.

In Step S310, the control unit 5 outputs an instruction signal to the display unit 6 to display characters, symbols or the like for notifying of occurrence of a system error. Then, the control ends.

On the other hand, if the intensity of the first reflected beam RL1 is larger than the first threshold (Step S307: No), the control returns to Step S301. At this time, the control unit 5 determines that the optical fiber 130 is not broken.

In the third control example, various effects similar to those of the first control example can be obtained. Furthermore, in the third control example, when the received light intensity of the second reflected beam RL2 is larger than the second threshold and the received light intensity of the first reflected beam RL1 is not more than the first threshold, it is determined that a system error has occurred in the detection system 10, the catheter device 100, or the laser ablation device 1000. As in the second control example, when the received light intensity of the first reflected beam RL1 is not more than the first threshold but the received light intensity of the second reflected beam RL2 is larger than the second threshold, it can be considered that such a state has a situation where some kind of system error has occurred. Therefore, in the third control example, it is determined that a system error has occurred, and the operator can be notified of the system error.

Fourth Control Example

Figure 6:
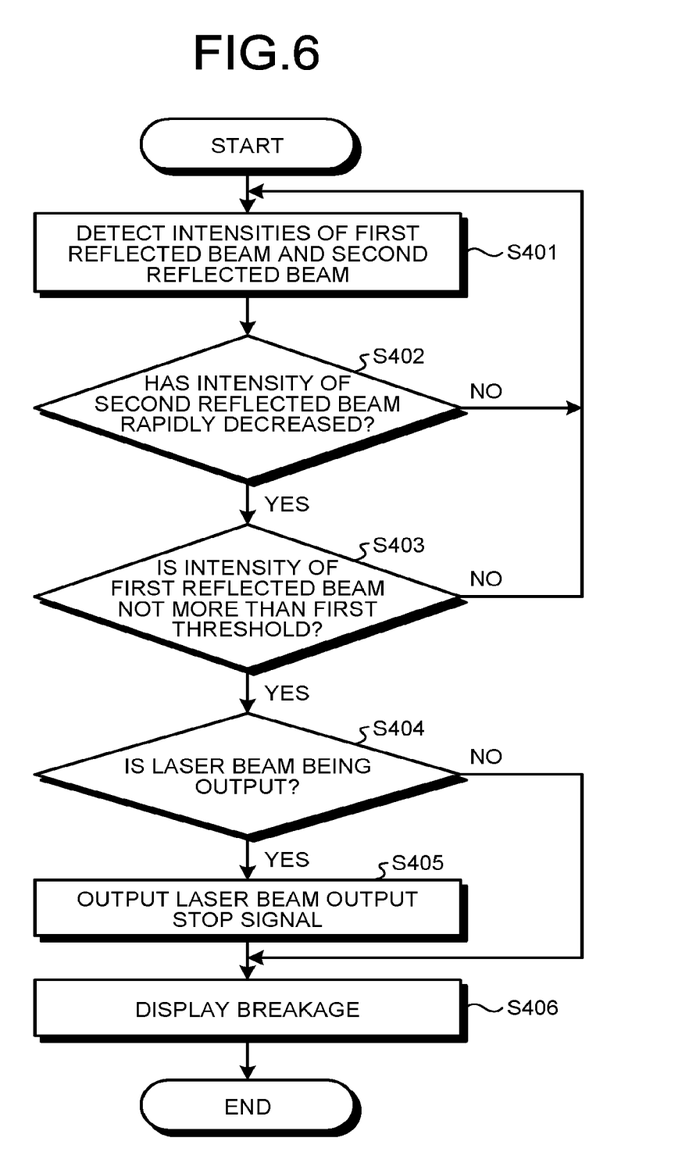
FIG. 6 is a flowchart of a fourth control example.

FIG. 6 is a flowchart of a fourth control example. This control process is performed in a state where the control unit 5 supplies the driving current to the LDs 1a and 1b, and the first test beam TL1 and the second test beam TL2 are output.

First, in Step S401, the control unit 5 detects the intensity of the first reflected beam RL1 and the intensity of the second reflected beam RL2. Subsequently, in Step S402, the control unit 5 determines whether the intensity of the second reflected beam RL2 rapidly decreases. If it is determined that the intensity of the second reflected beam RL2 does not rapidly decrease (Step S402: No), the control returns to Step S401. If it is determined that the intensity of the second reflected beam RL2 rapidly decreases (Step S402: Yes), the control proceeds to Step S403.

For example, the rapid decrease is determined as follows. In other words, the control unit 5 repeats the detection of the intensity of the first reflected beam RL1 and the intensity of the second reflected beam RL2 in Step S401 in a predetermined time period, and when a decrease in the intensity of the second reflected beam RL2 per time period is not less than a predetermined amount, it is determined that the intensity of the second reflected beam RL2 has rapidly decreased. Note that the criterion for determining the rapid decrease of the intensity of the second reflected beam RL2 is not limited to this description. For example, in a case where the catheter device 100 includes a mechanism for detecting an insertion length of the catheter portion 110 inserted into the body, it may be determined that the intensity of the second reflected beam RL2 has rapidly decreased, when a decrease in the intensity of the second reflected beam RL2 per unit insertion length is not less than a predetermined amount.

Subsequently, in Step S403, the control unit 5 determines whether the intensity of the first reflected beam RL1 is not more than the first threshold. If the intensity of the first reflected beam RL1 is not more than the first threshold (Step S403: Yes), the control proceeds to Step S404. At this time, the control unit 5 determines that the optical fiber 130 is broken.

In Step S404, the control unit 5 determines whether the laser beam AL is being output. If the laser beam AL is being output (Step S404: Yes), the control proceeds to Step S405. In Step S405, the control unit 5 outputs the laser beam output stop signal to the laser beam source. If the laser beam AL is not output (Step S404: No) or after the end of Step S405, the control proceeds to Step S406.

In Step S406, the control unit 5 causes the display unit 6 to display characters, symbols or the like for notifying of the breakage of the optical fiber 130 Then, the control ends.

On the other hand, if the intensity of the first reflected beam RL1 is larger than the first threshold (Step S403: No), the control returns to Step S401. At this time, the control unit 5 determines that the optical fiber 130 is bent.

In the fourth control example, the breakage and the bending of the optical fiber 130 can be effectively distinguished and detected. Furthermore, in the fourth control example, the effect of preventing the laser beam AL from being unintentionally output from the broken portion of the optical fiber 130 can be obtained. Furthermore, when it is determined that the optical fiber 130 is broken, the effect can be obtained that the operator of the laser ablation device 1000 can be notified of the breakage of the optical fiber 130.

Note that, to the third control example and the fourth control example, as in the first control example, control may be added that when the received light intensity of the first reflected beam RL1 is larger than the first threshold and the intensity of the second reflected beam RL2 is not more than the second threshold, it is determined that the optical fiber 130 is bent with an amount of bending not less than a predetermined amount of bending and the operator is notified of the bending.

Note that, to the second, third, and fourth control examples, as in the first control example, control may be added that when the received light intensity of the first reflected beam RL1 is larger than the first threshold and the intensity of the second reflected beam RL2 is not more than the bending threshold, it is determined that the optical fiber 130 is bent with an abnormal amount of bending in the abnormal state and the operator is notified of the bending.

Furthermore, in the fourth control example, rapid decrease of the intensity of the second reflected beam RL2 and the intensity of the first reflected beam RL1 that is larger than the first threshold show that the optical fiber 130 is bent with a small bend radius. In a case where the catheter device 100 including the present detection system 10 is a catheter device to be inserted into blood vessel, this situation indicates that the distal end portion of the catheter portion 110 is approaching a sharply bending portion of the blood vessel. Information about the amount of bending can be obtained from a state of decrease in the second reflected beam RL2. This also makes it possible to obtain, on the basis of the information about the amount of bending, information about the shape of a blood vessel in which the distal end portion of the catheter portion 110 is located, that is, information about the shape of a target into which the optical fiber is inserted.

In the embodiments described above, the detection system includes two light sources and two light receiving units, but the detection system may include three or more light sources and three or more light receiving units. In this configuration, the respective light sources output test beams that have different wavelengths and provide different bending losses of the optical fiber. The reflector reflects each of the test beams propagating through the optical fiber near the distal end portion of the optical fiber. Each of the light receiving units receives each of a plurality of reflected beams, which are beams reflected by the reflector, near the proximal end portion. The determination unit determines whether the optical fiber is bent or broken on the basis of the received light intensity of a reflected beam at each of the light receiving units. For the light sources, a broadband light source that outputs broadband light may be employed. When the broadband light source is employed, only one light source may be used. In this configuration, a plurality of wavelength components included in the broadband light corresponds to the plurality of test beams. This configuration employs a reflector or a bandpass filter that is suitable for using the broadband light source.

For example, a description will be made of a configuration that includes three light sources and three light receiving units and uses three test beams (a first test beam having a wavelength λ1, a second test beam having a wavelength λ2, and a third test beam having a wavelength λ3). It is assumed that λ1<λ2<λ3 holds in wavelength, where λ1 is set in a 400 nm band, λ2 is set in a 1300 nm band, and λ3 is set in a 1500 nm band. In this case, breakage of the optical fiber can be detected with the first test beam, bending thereof having a bending diameter of 12 mm or less can be detected with the second test beam, and bending thereof having a bending diameter of 16 or less can be detected with the third test beam. In this way, the bend radius can be estimated in more detail by using a plurality of test beams having different wavelengths and providing different bending losses.

Furthermore, in the embodiments described above, the reflector is constituted by one FBG, but the reflector may be constituted by one reflecting film. In addition, the detection system may include a plurality of reflectors so as to reflect the plurality of test beams to generate a plurality of reflected beams. When the plurality of reflectors are provided, for example, one reflector may include a reflecting film and the other may include an FBG. Such a reflecting film can be provided at the distal end portion 132 of the optical fiber 130 or on an end surface of the FBG.

Here, the reflector preferably has a reflectivity that is higher than that of the Fresnel reflection caused by air. For example, the reflector preferably has a configuration to reflect 40% or more of a test beam, that is, 10 times the reflectivity of the Fresnel reflection caused by air. The reflection band of the reflector is not particularly limited, but when the broadband light source is used as the light source, at least two wavelength components need to be separated and reflected. For example, when the reflector includes a plurality of FBGs, the reflection bandwidth includes, but is not particularly limited, to a bandwidth of plus or minus 10 nm about a central reflection wavelength, having a configuration in which part of the 1300 nm band and part of the 1500 nm band are reflected.

Furthermore, the reflector may include, for example, a bandpass filter that transmits only the wavelength of the laser beam AL and reflects the other wavelengths, having a configuration to reflect a plurality of test beams.

Furthermore, in the embodiments described above, both the first light receiving unit and the second light receiving unit are configured by the PDs, but one of the first light receiving unit and the second light receiving unit may be configured by the PD.

Furthermore, in the embodiments described above, in order to detect the abnormal state in which the catheter portion 110 is inserted into the wrong portion, the intensity of the second reflected beam is used for the detection of the abnormal state, but the intensity of the first reflected beam may be used for the detection of the abnormal state.

In the embodiments described above, the reference set values are stored in the storage unit, but the reference set values can be held by another method. Specifically, it is possible to hold a value after conversion by an AD converter in a circuit inside the control unit 5. Furthermore, application of a voltage or the like corresponding to a threshold for determination of breakage to a circuit inside the control unit 5, with the circuit as an analog circuit, makes it possible to hold a reference set value (first threshold) for determination of the breakage in the circuit. Furthermore, reference set values (bending threshold, second threshold, third threshold) for determination of bending may be stored in the storage unit as a table or functional expressions.

Although the FBG7 is used as the reflector in the embodiments described above, the reflector may be constituted by a reflecting film. When the reflector is constituted by the reflecting film, the detection system 10 according to an embodiment has an effect of dependence on no external environment. Furthermore, when the reflector is constituted by the reflecting film, the reflector can be used without adjustment, even in a gas or a liquid such as blood that is a substance having a different refractive index. Furthermore, when the reflector is constituted by a material other than the reflecting film, use of Fresnel reflection makes it possible for the detection system 10 to determine whether the reflector is used in the air or in the liquid, and thus, the reflector can be used as a fluid detector.

Furthermore, when, as the optical fiber 130, an optical fiber having cores concentrically provided is used and a beam propagating through a single mode (SM) portion constituted by a core located at the center of the cross-section of the optical fiber 130 is used to detect the amount of bending, mode dependence can be reduced, and the accuracy in detecting the amount of bending can be improved. On the other hand, a beam emitted from a multi-mode (MM) portion constituted by a core having a diameter larger than the SM portion can be used as an ablation beam. In the optical fiber 130 configured as described above, when sensitivity is emphasized, a beam used for detecting breakage is set so that a fundamental mode (Gaussian mode) is dominant and a beam used for detecting the amount of bending may be set so that a higher-order mode such as a cladding mode is dominant. The higher mode is more sensitive to bending than the fundamental mode, and thus, the sensitivity can be improved. On the other hand, when accuracy is emphasized, it is preferable for the beam used for detecting breakage to be set so that the higher-order mode is dominant and for the beam used for detecting the amount of bending to be set so that the fundamental mode is dominant. Accordingly, for the fundamental mode, the mode dependence in bending loss does not need to be considered, improving the accuracy.

Furthermore, the present disclosure is not limited to the embodiments described above. Any appropriate combination of component elements described in the above embodiments are also included within the scope of the present disclosure. Furthermore, further effects and modifications are readily conceivable by those skilled in the art. Therefore, the broader aspects of the present disclosure are not limited to the embodiments described above, and various modifications and alterations can be made.

The detection system, the catheter device, and the laser ablation device according to the present disclosure are useful for inserting the catheter into a patient's body, irradiating a target portion such as an affected area with an ablation laser beam output from the distal end of the optical fiber, and for treatment.

According to the present disclosure, it is possible to effectively detect a state of an optical fiber and a state around the optical fiber.

Although the disclosure has been described with respect to specific embodiments for a complete and clear disclosure, the appended claims are not to be thus limited but are to be construed as embodying all modifications and alternative constructions that may occur to one skilled in the art that fairly fall within the basic teaching herein set forth.

The invention claimed is:

1. A laser ablation device for outputting an ablation laser beam from a distal end of an optical fiber and irradiating a target area with the ablation laser for treatment, comprising:
   a laser beam source that outputs the ablation laser beam input to a proximal end portion side of the optical fiber;

at least one light source that outputs a plurality of test beams input to the proximal end portion side of an optical fiber and having different wavelengths and providing different bending losses of the optical fiber;

at least one reflector that reflects each of the test beams propagating through the optical fiber, on a distal end portion side of the optical fiber;

a plurality of light receivers arranged to receive a plurality of reflected beams each being a beam reflected by the at least one reflector, on the proximal end portion side;

a first optical multiplexer/demultiplexer configured to multiplex the plurality of test beams;

a second optical multiplexer/demultiplexer configured to demultiplex the plurality of reflected beams; and a determination unit comprising a calculation unit and storage unit which are configured so that the determination unit, based on information about the reflected beams at the plurality of light receivers, compares the information about the reflected beams with reference set values, wherein the information about the reflected beams includes received light intensities of the reflected beams at the light receivers, and the reference set values are thresholds of the received light intensities, and the determination unit is configured so that it determines whether the optical fiber is bent or broken based on the received light intensities of the reflected beams.

2. The device according to claim 1, wherein the determination unit is configured so that it:

determines that the optical fiber is broken, when a received light intensity of a first reflected beam, of the plurality of reflected beams, is not more than a first threshold, the first reflected beam being a reflected beam from a first test beam;

determines that the optical fiber is not broken, when the received light intensity of the first reflected beam is larger than the first threshold; and determines that the optical fiber is bent with an amount of bending not less than a predetermined amount of bending, when the received light intensity of the first reflected beam is larger than the first threshold and a received light intensity of a second reflected beam, of the plurality of reflected beams, is not more than a second threshold, the second reflected beam being a reflected beam from a second test beam provides a larger bending loss in the optical fiber than the first test beam does.

3. The device according to claim 1, wherein when a received light intensity of a second reflected beam of the plurality of reflected beams has rapidly decreased, the second reflected beam being a reflected beam from a second test beam, the determination unit is configured so that it:

determines that the optical fiber is broken, when a received light intensity of a first reflected beam is not more than a first threshold, the first reflected beam being a reflected beam from a first test beam provides a smaller bending loss in the optical fiber than the second test beam does; and determines that the optical fiber is bent, when the received light intensity of the first reflected beam is larger than the first threshold.

4. The device according to claim 3, wherein when the received light intensity of the second reflected beam has rapidly decreased, information about an amount of bending is obtained from a state of decrease in the second reflected beam, when the received light intensity of the first reflected beam is larger than the first threshold.

5. The device according to claim 1, comprising a plurality of the reflectors, at least one of which includes a fiber Bragg grating.

6. The device according to claim 1, comprising a plurality of the reflectors, at least one of which includes a reflecting film.

7. The device according to claim 1, wherein
at least one of the plurality of light receivers is a photodiode.

8. A catheter device comprising:
the laser ablation device according to claim 1;
the optical fiber to which the plurality of test beams are input from the proximal end portion side, and in which the at least one reflector is provided on the distal end portion side; and
a catheter body into which at least a part of the optical fiber is inserted.

9. The laser ablation device of claim 1, wherein the determination unit is further configured to detect a degree of bending of the optical fiber based on the information about the reflected beams at the plurality of light receivers.

10. The laser ablation device of claim 1, wherein the at least one light source simultaneously outputs a plurality of test beams input to the proximal end portion side of an optical fiber and having different wavelengths and providing different bending losses of the optical fiber.

11. The laser ablation device of claim 10, further comprising a multiplexer configured to multiplex the plurality of test beams with the ablation laser beam.

* * * * *